United States Patent
Haueter et al.

(10) Patent No.: US 8,560,131 B2
(45) Date of Patent: Oct. 15, 2013

(54) METHOD FOR SETTING A BASAL RATE PROFILE FOR AN INSULIN PUMP

(75) Inventors: Ulrich Haueter, Schweiz (CH); Thomas Vering, Schweiz (CH); Daniel von Büren, Sierentz (FR)

(73) Assignee: Roche Diagnostics International AG, Rotkreuz (CH)

( * ) Notice: Subject to any disclaimer, the term of this patent is extended or adjusted under 35 U.S.C. 154(b) by 409 days.

(21) Appl. No.: 12/580,580

(22) Filed: Oct. 16, 2009

(65) Prior Publication Data

US 2010/0082167 A1 Apr. 1, 2010

Related U.S. Application Data

(63) Continuation of application No. PCT/CH2008/000138, filed on Mar. 28, 2008.

(30) Foreign Application Priority Data

Apr. 19, 2007 (EP) .................................... 07007991

(51) Int. Cl.
 *G05D 7/06* (2006.01)
 *G06F 17/17* (2006.01)
(52) U.S. Cl.
 USPC .......................................... 700/282; 700/290
(58) Field of Classification Search
 None
 See application file for complete search history.

(56) References Cited

U.S. PATENT DOCUMENTS

| 5,088,981 | A | 2/1992 | Howson et al. |
| 7,347,854 | B2 * | 3/2008 | Shelton et al. ............. 604/891.1 |
| 7,651,845 | B2 * | 1/2010 | Doyle et al. .................... 435/14 |
| 7,655,618 | B2 * | 2/2010 | Green et al. .................. 514/1.1 |
| 7,766,829 | B2 * | 8/2010 | Sloan et al. .................. 600/309 |
| 2004/0055611 | A1 | 3/2004 | Penny et al. |
| 2005/0272640 | A1 | 12/2005 | Doyle, III et al. |
| 2006/0009734 | A1 | 1/2006 | Martin |
| 2009/0247857 | A1* | 10/2009 | Harper et al. ................. 600/365 |

FOREIGN PATENT DOCUMENTS

| EP | 0002776 | 7/1979 |
| EP | 0164904 A2 | 12/1985 |
| WO | 9636389 A1 | 11/1996 |

OTHER PUBLICATIONS

International Search Report, Appl. No. PCT/CH2008/000138, Apr. 19, 2007, 4 pages.

* cited by examiner

*Primary Examiner* — Kakali Chaki
*Assistant Examiner* — Walter Hanchak
(74) *Attorney, Agent, or Firm* — Dinsmore & Shohl LLP

(57) ABSTRACT

Methods for setting a basal rate profile for an insulin pump with an input unit and a calculation unit are disclosed. A number of interpolation nodes for the basal rate profile are defined by means of the input unit of the insulin pump. A continuous function with respect to the interpolation nodes, which images the interpolation nodes and any previously stored basal rates, is formed using the calculation unit of the insulin pump, and a temporal sequence of basal rates to be released by the insulin pump during specific time intervals is generated from the continuous function using the calculation unit of the insulin pump.

18 Claims, 3 Drawing Sheets

METHOD FOR SETTING A BASAL RATE PROFILE FOR AN INSULIN PUMP

CROSS-REFERENCE TO RELATED APPLICATIONS

This application is a continuation of international application PCT/CH2008/000138, which was filed on 28 Mar. 2008, and claims the priority of European Patent Application 07 007 991.8, which was filed on 19 Apr. 2007, and the entire disclosure of which is herewith incorporated by reference.

TECHNICAL FIELD

Embodiments of the invention relate generally to insulin pumps, and particularly to a method for setting a basal rate profile for an insulin pump with an input unit and a calculation unit.

BACKGROUND

U.S. Pat. No. 6,810,290 B2 discloses a method for setting basal rates for an implantable insulin pump in which, when the basal rates to be released by the insulin pump are changed, not all basal rates, but only the basal rates to be changed have to be reset. The reset is effected by specifying the basal rate and the start time of the release.

SUMMARY

Embodiments of the invention relates to a method for setting a basal rate profile for an insulin pump with an input unit and a calculation unit. A number of interpolation nodes for the basal rate profile are defined by means of the input unit of the insulin pump. A continuous function with respect to the interpolation nodes, which images the interpolation nodes and any previously stored basal rates, is formed using the calculation unit of the insulin pump, and a temporal sequence of basal rates to be released by the insulin pump during specific time intervals is generated from the continuous function using the calculation unit of the insulin pump.

In one particular embodiment, a method for setting a basal rate profile for an insulin pump with an input unit and a calculation unit is disclosed. The method comprises defining a number of interpolation nodes for the basal rate profile by means of the input unit of the insulin pump, an interpolation node being defined by a start time of a basal rate release and a basal rate to be released associated with this start time or an absolute or relative amount of insulin to be released associated with this start time; forming a continuous function with respect to the interpolation nodes by interpolation and/or approximation using the calculation unit of the insulin pump, the function imaging the interpolation nodes; and generating a temporal sequence of basal rates to be released by the insulin pump during specific time intervals from the continuous function using the calculation unit of the insulin pump, the continuous function for generating the temporal sequence of basal rates using the calculation unit being discretized.

In another embodiment, a method for setting a basal rate profile for an insulin pump with an input unit and a calculation unit is disclosed. The method comprises defining a number of interpolation nodes for the basal rate profile by means of the input unit of the insulin pump, an interpolation node being defined by a start time of a basal rate release and a basal rate to be released associated with this start time or an absolute or relative amount of insulin to be released associated with this start time; comparing the defined interpolation nodes to predefined interpolation nodes and any previously stored basal rates of a stored basal rate profile; generating a warning signal in the case where the defined interpolation nodes deviate from the predefined interpolation nodes and the previously stored basal rates by more than a predefined value; forming, only in the case where the defined interpolation nodes deviate by no more than the predefined value from the predefined interpolation nodes and the previously stored basal rates, a continuous function with respect to the interpolation nodes by interpolation and/or approximation using the calculation unit of the insulin pump, the function imaging the defined interpolation nodes and the previously stored basal rates; and generating a temporal sequence of basal rates to be released by the insulin pump during specific time intervals from the continuous function when formed by using the calculation unit of the insulin pump, the continuous function for generating the temporal sequence of basal rates using the calculation unit being discretized.

Further advantageous refinements of the invention emerge from the dependent claims and the exemplary embodiments illustrated below with reference to the drawings.

BRIEF DESCRIPTION OF THE DRAWINGS

In the figures, the same reference symbols designate structurally or functionally equivalent components, and in which.

DETAILED DESCRIPTION

Figure 1:
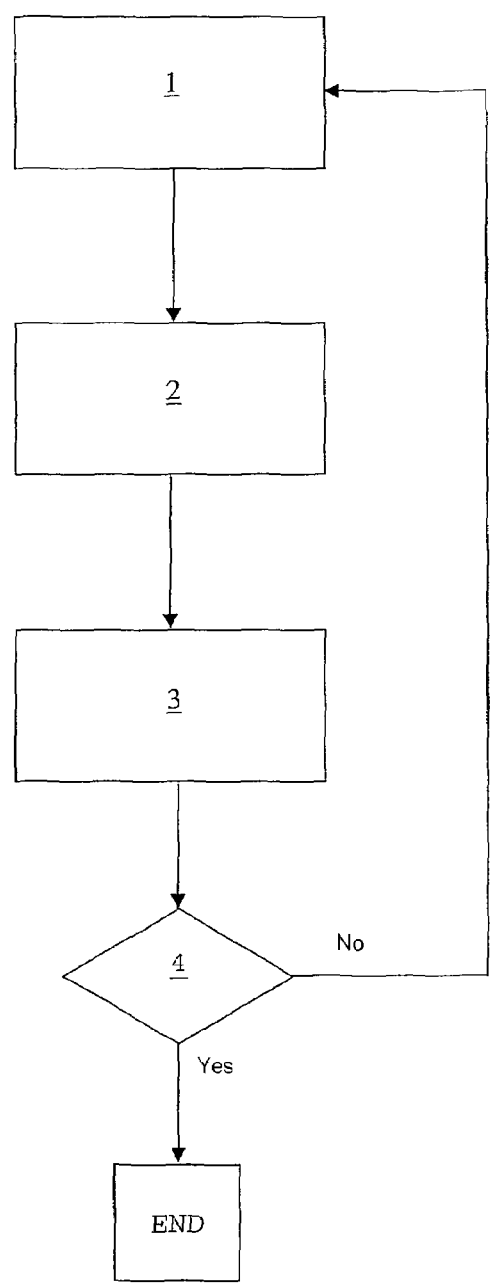
FIG. 1 shows a flowchart of a method according to the invention.

Embodiments of the invention provide a simple method for setting a physiological basal rate profile for an insulin pump. A physiological basal rate profile is, in particular, understood to mean a release profile which is as continuous as possible.

In one embodiment, a method according to the invention for setting a basal rate profile for an insulin pump with an input unit and a calculation unit is characterized in that a number of interpolation nodes for the basal rate profile are defined by means of the input unit of the insulin pump, a continuous function with respect to the interpolation nodes, which images the interpolation nodes and preferably basal rates of a stored basal rate profile, which basal rates have possibly already been stored, is formed using the calculation unit of the insulin pump and a temporal sequence of basal rates to be released by the insulin pump during specific time intervals is generated from the continuous function using the calculation unit of the insulin pump. The temporal sequence represents the basal rate profile. The basal rate profile is preferably stored in a memory unit which is assigned to the insulin pump and preferably forms part of the insulin pump.

The term "setting a basal rate profile" can also be understood to mean generating or storing a basal rate profile.

An interpolation node is defined by the start time of a basal rate release, and the basal rate to be released associated with this start time or the absolute or relative amount of insulin to be released associated with this start time. The basal rate is considered to be that amount of insulin which is required to keep the glucose metabolism of a patient stable—excluding additional influences through food ingestion or extraordinary, glucose-burning activities such as physical activities. The input unit and the calculation unit of the insulin pump can be arranged both outside the insulin pump and within the insulin pump itself.

The method according to the invention makes it possible to set a complete physiological basal rate profile, as is the case, for example, at the beginning of a therapy or when there are relatively large changes in the therapy and hence there basically is a complete change in the basal rate profile. Furthermore, in the case of a previously stored basal rate profile, the method according to the invention makes it possible to easily obtain physiologically correct changes or adaptations of the stored basal rate profile by defining individual interpolation nodes or a single interpolation node. By way of example, this permits fine-tuning of the stored basal rate profile.

A basal rate profile usually covers a time period of 24 hours, with typically each hour being associated with a basal rate so that the basal rate profile is formed by a temporal sequence of 24 basal rates. Alternatively, it is also possible for each half hour to be associated with a basal rate so that the basal rate profile is formed by a temporal sequence of 48 basal rates. Accordingly, such a temporal sequence can also be formed from a different number of basal rates, such as, for example, 12 or 96 basal rates.

In accordance with one refinement of the invention, four to ten interpolation nodes are defined for the basal rate profile. The interpolation nodes are defined by input using the input unit of the insulin pump, with preferably the start time of a basal rate release and the basal rate to be released associated with this start time being input for every interpolation node to be defined. The interpolation nodes are generally defined for a basal rate profile which covers a time period of 24 hours. However, it is also possible to define interpolation nodes for a basal rate profile which covers a time period of a number of days, for example a week or a month, as can be the case in e.g. a bio-rhythmical profile. The number of defined interpolation nodes can then be increased correspondingly.

A continuous function is formed with respect to the interpolation nodes, preferably by means of interpolation and/or approximation, which function images the interpolation nodes or the interpolation nodes and possibly previously stored basal rates. That is to say that the interpolation nodes or the interpolation nodes and possibly previously stored basal rates are connected to one another by means of a suitable continuous curve. By way of example, linear interpolation can be used, in which a linear polynomial is selected as a trial function to solve the underlying interpolation problem. Trigonometric interpolation is preferably used, in which a trigonometric polynomial, e.g. a sine and/or cosine function, is used as a trial function for a function to connect the interpolation nodes. As a result of applying trigonometric interpolation, it is possible to obtain a continuous or harmonic continuous function and hence a basically more continuous or more harmonic change of the basal rate. Moreover, it is also possible to use so-called splines as trial functions for the interpolation.

In order to generate a temporal function of basal rates from the continuous function, the continuous function is discretized using the calculation unit. During the discretization, the time period of the continuous function is divided into a finite number of time intervals adjoining one another, with each time interval being assigned a value of the continuous function. The assigned value of the continuous function can, for example, be the value at the beginning of the respective time interval or the value lying in the middle of the respective time interval. The value assigned to the respective time interval forms the basal rate to be released to the patient by the insulin pump during the respective time interval. The number of the basal rates of the generated temporal sequence is preferably greater than the number of defined or input interpolation nodes. The method according to the invention then advantageously generates a basal rate profile from a few input interpolation nodes—and possibly additionally from previously stored basal rates—which also contains basal rates which lie between the basal rates formed by the interpolation nodes. That is to say that intermediate values for basal rates lying between the interpolation nodes are generated using the method according to the invention.

The basal rate to be released remains constant during the respective time intervals. The basal rate to be released is preferably defined in the unit IE/hour, with 1 IE corresponding to 41.67 µg insulin (highly pure) or 35 µg insulin (anhydrous). The unit IE is the international unit for the amount of a substance, which is often abbreviated IU (international unit) in the English-speaking world.

By generating a temporal sequence from the continuous function by means of discretization, it is possible to display to the patient or the user of the insulin pump the currently released amount of insulin by means of a display unit, also called display, which is possibly assigned to the insulin pump, for example, because such a display unit can often only display discrete values and not continuous functions.

The temporal sequence of basal rates to be released can comprise 24 basal rates, with each basal rate intended to be released by the insulin pump over a time period of 1 hour. However, it is also possible to generate less than 24 basal rates during the generation of the temporal sequence so that, for example, a basal rate is in each case released over a time period which is longer than 1 hour. It is also possible to generate more than 24 basal rates so that in the case of a total release time range of 24 hours, a basal rate is for example released for less than 1 hour. The time intervals in which the basal rates are intended to be released to the patient can be equidistant, but they can also be of different lengths so that, for example, a first basal rate of the temporal sequence is released for 15 minutes, while a second basal rate is released for 3 hours.

The continuous function with respect to the interpolation nodes is preferably formed such that an interpolation node whose value lies between two lower-lying interpolation nodes forms a maximum of the continuous sequence, while an interpolation node which lies between two higher-lying interpolation nodes in terms of value forms a minimum of the continuous function. This can advantageously prevent overshoots or undershoots in the interpolation, which could occur, for example, in the case of an interpolation using a spline function. Furthermore, when forming the continuous function, interpolation nodes with the same values are preferably connected by means of a straight line, that is to say horizontally. If neighbouring interpolation nodes have different values, and one interpolation node defines a minimum and the neighbouring interpolation node defines a maximum of the continuous function, the continuous function preferably has precisely one turning point between the minimum and the maximum. The turning point preferably lies in the centre between the two interpolation nodes, both in terms of time and amplitude, the amplitude in particular corresponding to the basal rate to be released.

The time intervals, into which the continuous function is subdivided in order to form the temporal sequence, are preferably selected such that in those time intervals in which the continuous function runs through an interpolation node, the interpolation node is placed in the centre of the time interval in terms of time.

When forming the continuous function, the last interpolation node with respect to its time or the last previously stored basal rate and the first interpolation node with respect to its time or the first previously stored basal rate are directly connected by the continuous function so that no discontinuous or non-physiological basal rate release is effected or the continuous function does not have a jump. The temporally last and temporally first interpolation nodes or stored basal rates are also referred to as wrap-around points. Hence, temporally, the time interval associated with the first basal rate of the temporal sequence immediately follows the time interval associated with the last basal rate. Hence, the basal rate profile formed by the temporal sequence of basal rates is run through without interruption and consistently run through back to back. The time range of the basal rate profile (or its time scale) can then, for example, also run from 5 o'clock to 5 o'clock rather than from midnight to midnight or can be selected in accordance with any other time range and be displayed to the user on a preferably provided display. In the case of a time scale from 5 o'clock in the morning to 5 o'clock in the morning, the whole night and the whole day can in each case be represented as an interrelated basal rate profile.

If the amount of infusion which is intended to be dispensed to a patient changes during, for example, a day, a week or a month, it is possible to proportionally adapt the individual basal rates of the basal rate profile in accordance with the change in the amount of infusion. By way of example, this can be effected by proportionally adapting the interpolation nodes, forming a continuous function from these proportionally adapted interpolation nodes and generating, once again, a temporal sequence of basal rates, i.e. a new basal rate profile, from this continuous function by discretization. This affords the possibility of a physiologically adequate and simultaneous adaptation of all basal rates or even of all stored basal rate profiles. The proportional adaptation of the interpolation nodes can be obtained by multiplying the values of the interpolation nodes by a factor which corresponds to the ratio between the previous total infusion amount and the new total infusion amount over the time range of the basal rate profile.

One or more basal rate profiles set or stored using the method according to the invention can be adapted with respect to their respective amplitude or profile depth by reapplying the method according to the invention and re-inputting one or more interpolation nodes, forming a new continuous function from these newly input interpolation nodes and the already stored unchanged interpolation nodes and/or the already stored basal rates of the stored temporal sequence and in turn generating a new temporal sequence of basal rates from said function. In this process, the amplitude of the basal rate profile can advantageously be changed by a corresponding change in the values of the interpolation nodes such that the total amount of infusion remains constant in the time range of the basal rate profile. If previously stored basal rates are used together with newly input interpolation nodes for forming a new temporal sequence of basal rates, those stored basal rates which are associated with those times associated with the newly input interpolation nodes are preferably not used.

Furthermore, a basal rate profile set or input previously with the aid of the method according to the invention can be displaced back and forth on the time scale or time axis, without the overall amount of infusion changing. This makes it possible to compensate for physiological-dependent insulin effect delays. In order to effect such a displacement, the input unit of the insulin pump preferably has corresponding buttons, so that, preferably, by actuating one button, insulin is dispensed in accordance with an undisplaced basal rate profile, while actuating another button dispenses insulin in accordance with a basal rate profile advanced by a certain period of time, for example an hour. Here, the undisplaced basal rate profile corresponds to a normal mode.

If the method according to the invention is used to reset or change a previously stored basal rate profile, the interpolation nodes can be defined by inputting percentage changes of at least a few of the previously stored or defined interpolation nodes and/or the previously stored basal rates via the input unit of the insulin pump or by inputting a new total infusion amount which is intended to be released over the time range or time duration of the basal rate profile, new or changed interpolation nodes being defined by the percentage deviation of the new total infusion amount compared to a previously stored total infusion amount.

In accordance with a particular refinement of the method according to the invention, the physiological plausibility of the set basal rate profile is determined by the calculation unit of the infusion pump determining the number of sign changes of the derivative of the continuous function and a warning signal being generated and/or the dispensing of insulin in accordance with the basal rate profile being prevented in the case where the number of sign changes exceeds a predefined limit value. The predefined limit value could have been stored or input by a user, for example prior to the first setting of a basal rate profile, by means of the input unit of the infusion pump. By way of example, the predefined limit value for the number of permitted sign changes can be 5.

In accordance with a further preferred refinement of the invention, the (newly) defined interpolation nodes are compared to previously predefined or stored interpolation nodes and/or to previously stored basal rates of the previously stored temporal sequence which correspond to the newly defined interpolation nodes of, for example, a previously stored basal rate profile, and only in the case where the defined interpolation nodes deviate by no more than a predefined value, in particular by no more than 20%, from the predefined or stored interpolation nodes and/or from the stored basal rates is a continuous function formed, and is a temporal sequence of basal rates to be released generated from the continuous function. A warning signal can be generated if the defined interpolation nodes deviate by more than the predefined value, in particular by more than 20%, from the predefined interpolation nodes and/or the stored basal rates. Provision can firstly be made for each newly defined interpolation node not being permitted to deviate by more than 20% from the predefined or stored interpolation node or stored basal rate corresponding to said newly defined node.

Alternatively, provision can be made for all newly defined interpolation nodes, that is to say the sum of their values, not being permitted to deviate by more than 20% from the stored interpolation nodes and/or the stored basal rates which correspond to the newly defined interpolation nodes, that is to say the sum of their values.

This leads to increased safety when using the infusion pump by there being a warning regarding physiologically unusual settings or by not using a physiologically unusual basal rate profile.

Approach(es) to Implement the Invention

FIG. 1 shows a flowchart of the method according to the invention. In a first method step 1, a number of interpolation nodes for the basal rate profile to be set are defined using an input unit of an insulin pump. To this end, the basal rate to be released and the start time for the release of the basal rate are input or defined. In a second method step 2, a continuous function with respect to the interpolation nodes, which function images the interpolation nodes, is formed using a calculation unit of the insulin pump—possibly taking into consideration previously stored basal rates of a previously stored basal rate profile. To this end, interpolation or approximation methods are preferably used. In a third method step 3, the basal rate profile is formed, using the calculation unit of the insulin pump, from the continuous function as a temporal sequence of basal rates to be released by the insulin pump during certain time intervals. The basal rate profile can then be displayed to the user on a preferably provided display and can be monitored in a method step 4. If the basal rate profile does not correspond or no longer corresponds to the user's ideas, or if the user wants to further change the basal rate profile, a jump is made to the first method step 1 and the user can change the basal rate profile by a renewed input of one or more interpolation nodes until a basal rate profile is generated which corresponds to said user's ideas (method step "End"). The change of a stored basal rate profile can also be effected by multiplying the stored basal rate profile by a factor predetermined or to be entered by the user so that the new interpolation nodes or the stored interpolation nodes multiplied by this factor or basal rates correspond.

Figure 2:
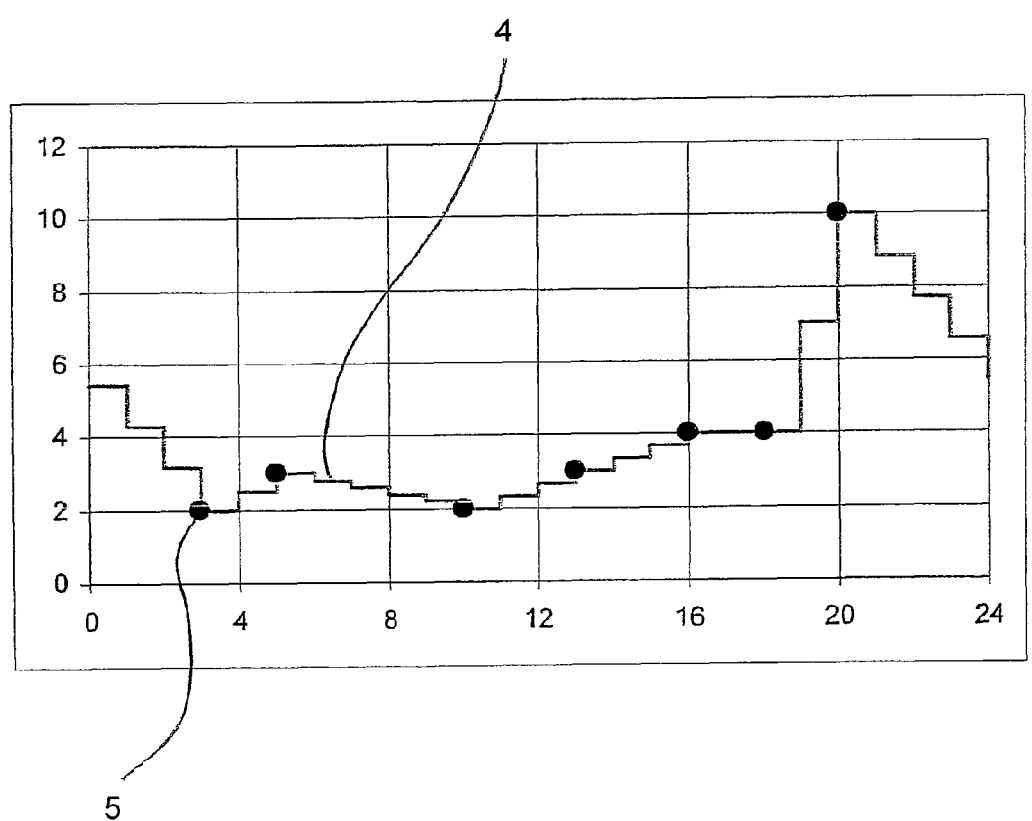
FIG. 2 shows a curve profile of a basal rate profile set using a method according to the invention.

FIG. 2 shows a basal rate profile 4 which was set using the method according to the invention and generated from interpolation nodes 5. A linear interpolation was used in the second method step 2 in order to form the continuous function, that is to say the interpolation nodes 5 were connected by linear polynomials during the interpolation, in this case by linear polynomials of the first order, i.e. straight lines. The time in hours is plotted on the abscissa, and the infusion amount in IE (international units, one IE corresponding to 41.67 µg insulin (highly pure) or 35 µg insulin (anhydrous)) is plotted on the ordinate. The time range of 24 hours was subdivided into time intervals of 1 hour each during the discretization of the continuous function in the third method step 3, and each of these time intervals was associated with the value of the basal rate at the beginning of the respective time interval. In this fashion, the step function illustrated in FIG. 2 is obtained as the basal rate profile. The basal rate value for the entire time interval assigned to an interpolation node is preferably respectively defined by the basal rate value at this interpolation node.

Figure 3:
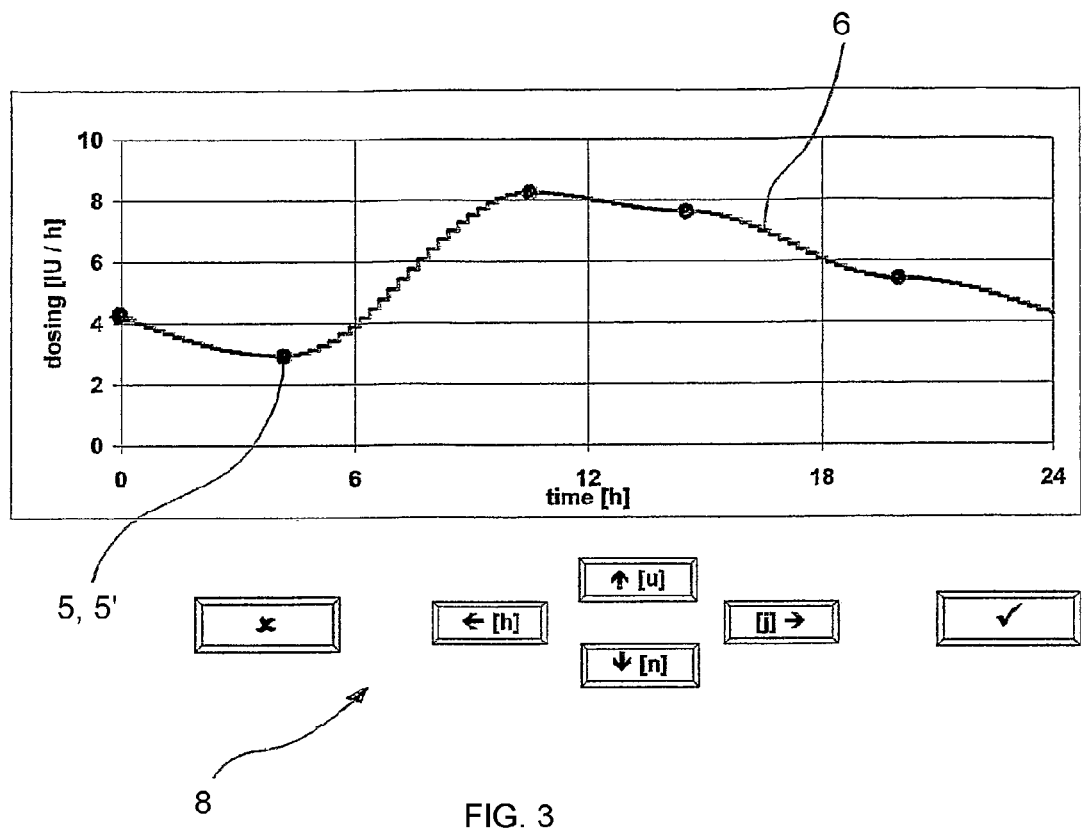
FIG. 3 shows a curve profile of a further basal rate profile set using a method according to the invention.
Figure 4:
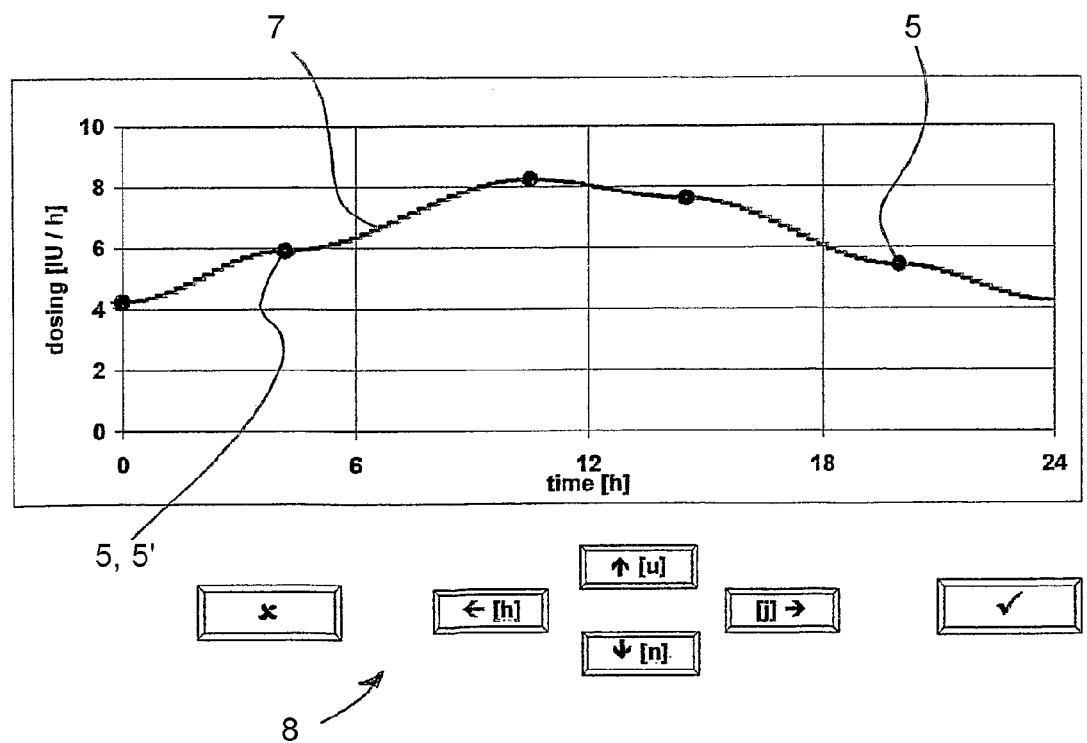
FIG. 4 shows the curve profile in accordance with FIG. 3 with a newly input or changed second interpolation node.

In the curve profiles of basal rate profiles illustrated in FIGS. 3 and 4, trigonometric polynomials, in particular a sine and/or cosine function, were used for the interpolation to form a continuous function from the respective interpolation nodes 5. The time in hours is once again illustrated on the abscissa in FIGS. 3 and 4, and the basal rate in the international unit IE, which is abbreviated IU in the English-speaking world, is again illustrated on the ordinate.

In the basal rate profile 7 illustrated in FIG. 4, the second interpolation node 5' in terms of time was, compared to the basal rate profile 6 illustrated in FIG. 3, increased in terms of value or the original second interpolation node 5' was deleted and a new interpolation node 5' was input. In accordance with the first method step 1 of the method according to the invention, this corresponds to a new definition of the second interpolation node 5'. Then the continuous function with respect to the interpolation nodes 5, 5', or with respect to the new interpolation node 5' and the previously stored basal rates which do not correspond to the original second interpolation node 5', is recalculated in the second method step 2. Then, the basal rate profile 7 as a temporal sequence of basal rates to be released at certain time intervals is generated from the continuous function in the third method step 3. In the curve profiles in FIGS. 3 and 4, the time intervals selected for the discretization in the third method step 3 are selected to be shorter than in the case of the curve profile according to FIG. 2.

The input unit of the insulin pump preferably has buttons 8 by means of which an interpolation node 5, 5' of the basal rate profile 6, 7 can be deleted (delete button "x"), by means of which an interpolation node 5, 5' of the basal rate profile 6, 7 can be entered (button provided with a tick), by means of which an interpolation node 5, 5' can be displaced upwards or downwards (buttons "u" or "n") and by means of which the entire basal rate profile 6, 7, or the interpolation nodes 5, 5' thereof, can be displaced to the left or right when viewed in time (buttons "h" and "j"). If a new basal rate profile is in particular calculated from newly input interpolation nodes 5, 5', which do not correspond to any previously stored interpolation nodes 5, 5', and possibly from previously stored basal rates, the delete button can be dispensed with.

Accordingly, a method for setting a basal rate profile (4, 6, 7) for an insulin pump with an input unit and a calculation unit, is characterized by the following steps: defining a number of interpolation nodes (5, 5') for the basal rate profile (4, 6, 7) by means of the input unit of the insulin pump, an interpolation node (5, 5') being defined by a start time of a basal rate release and a basal rate to be released associated with this start time or an absolute or relative amount of insulin to be released associated with this start time; forming a continuous function with respect to the interpolation nodes (5, 5') by interpolation and/or approximation using the calculation unit of the insulin pump, said function imaging the interpolation nodes (5, 5'); and generating a temporal sequence (4, 6, 7) of basal rates to be released by the insulin pump during specific time intervals from the continuous function using the calculation unit of the insulin pump, the continuous function for generating the temporal sequence (4, 6, 7) of basal rates using the calculation unit being discretized.

While in the present application preferred embodiments of the invention are described, it has to be explicitly mentioned that the invention is not limited to these and can also be effected in another form within the scope of the following claims.

What is claimed is:

1. A method for setting a basal rate profile for an insulin pump with an input unit and a calculation unit, comprising:
defining a number of interpolation nodes for the basal rate profile by means of the input unit of the insulin pump, an interpolation node being defined by a start time of a basal rate release and a basal rate to be released associated with this start time or an absolute or relative amount of insulin to be released associated with this start time;
forming a continuous function with respect to the interpolation nodes by interpolation and/or approximation using the calculation unit of the insulin pump, said function imaging the interpolation nodes by connecting each interpolation node to the previous interpolation node and subsequent interpolation node by a continuous curve; and
generating a temporal sequence of basal rates to be released by the insulin pump during specific time intervals from the continuous function using the calculation unit of the insulin pump, the continuous function for generating the temporal sequence of basal rates using the calculation unit being discretized.

2. A method according to claim 1, wherein the continuous function images stored basal rates in addition to the interpolation nodes.

3. A method according to claim 1, wherein four to ten interpolation nodes are defined.

4. A method according to claim 1, wherein at least 24 basal rates are generated.

5. A method according to claim 1, wherein less than 24 basal rates are generated, the number of the generated basal rates being greater than the number of the defined interpolation nodes.

6. A method according to claim 1, wherein, temporally, the time interval associated with the first basal rate of the temporal sequence immediately follows the time interval associated with the last basal rate.

7. A method according to claim 1, wherein a number of sign changes of the derivative of the continuous function is determined by the calculation unit and a warning signal is generated in the case where the number of sign changes exceeds a predetermined limit value.

8. A method according to claim 7, wherein the predetermined limit value is five.

9. A method according to claim 1, further comprising comparing the defined interpolation nodes to at least one of predefined interpolation nodes and any previously stored basal rates of a stored basal rate profile.

10. A method according to claim 9, wherein the continuous function is formed only in the case where the defined interpolation nodes deviate by no more than a predefined value from at least one of the predefined interpolation nodes and the previously stored basal rates of the stored basal rate profile.

11. A method according to claim 10, wherein the predefined value is no more than 20 percent.

12. A method according to claim 10, wherein the continuous function images the defined interpolation nodes and the previously stored basal rates.

13. A method according to claim 1, wherein the defined interpolation nodes are compared to at least one of predefined interpolation nodes and stored basal rates, and a warning signal is generated in the case where the defined interpolation nodes deviate from at least one of the predefined interpolation nodes and the stored basal rates by more than a predefined value.

14. A method according to claim 13, wherein the deviation is by more than 20 percent.

15. A method for setting a basal rate profile for an insulin pump with an input unit and a calculation unit, comprising:

defining a number of interpolation nodes for the basal rate profile by means of the input unit of the insulin pump, an interpolation node being defined by a start time of a basal rate release and a basal rate to be released associated with this start time or an absolute or relative amount of insulin to be released associated with this start time;

comparing the defined interpolation nodes to predefined interpolation nodes and any previously stored basal rates of a stored basal rate profile;

generating a warning signal in the case where the defined interpolation nodes deviate from the predefined interpolation nodes and the previously stored basal rates by more than a predefined value;

forming, only in the case where the defined interpolation nodes deviate by no more than the predefined value from the predefined interpolation nodes and the previously stored basal rates, a continuous function with respect to the interpolation nodes by interpolation and/or approximation using the calculation unit of the insulin pump, said function imaging the defined interpolation nodes and the previously stored basal rates by connecting each interpolation node to the previous interpolation node and subsequent interpolation node by a continuous curve; and generating a temporal sequence of basal rates to be released by the insulin pump during specific time intervals from the continuous function when formed by using the calculation unit of the insulin pump, the continuous function for generating the temporal sequence of basal rates using the calculation unit being discretized.

16. A method according to claim 15, wherein the predefined value is 20 percent.

17. A method according to claim 15, further comprising determining a number of sign changes of the derivative of the continuous function by using the calculation unit and generating a warning signal in the case where the number of sign changes exceeds a predetermined limit value.

18. A method according to claim 17, wherein the predetermined limit value is five.

* * * * *